(12) United States Patent
Gibbs

(10) Patent No.: US 6,586,461 B1
(45) Date of Patent: Jul. 1, 2003

(54) PRENYL TRANSFERASE INHIBITORS

(75) Inventor: Richard A. Gibbs, Detroit, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 09/334,704

(22) Filed: Jun. 16, 1999

Related U.S. Application Data
(60) Provisional application No. 60/089,625, filed on Jun. 16, 1998.

(51) Int. Cl.$^7$ .................... A61K 31/341; A61K 31/381; C07D 307/38; C07D 333/10; C07F 9/06
(52) U.S. Cl. .................... 514/438; 514/461; 549/79; 549/497; 558/152; 568/715
(58) Field of Search .................... 549/78, 497; 558/152; 568/14, 715, 807; 514/438, 461

(56) References Cited

U.S. PATENT DOCUMENTS

| | | | |
|---|---|---|---|
| 5,362,906 A | 11/1994 | Anthony et al. | 562/23 |
| 5,567,729 A | 10/1996 | Bradfute et al. | 514/546 |
| 5,602,184 A | 2/1997 | Myers et al. | 514/739 |

OTHER PUBLICATIONS

Koyama et al., Biochim Biophys. Acta, vol. 617(2) pp. 218–224, 1980.*
Nagano et al, Bull. Chem. Soc. Jpn., vol. 69(7) pp. 2071–2078, 1996.*
Mu et al., J. Org. Chem., vol. 61(23) pp. 8010–8015, 1996.*
Sen et al., J. Org. Chem., vol. 62(11) pp. 3529–3536, 1997.*
Dawe et al., Biochemistry, vol. 36(40) pp 12036–12044, 1997.*
Burke, et al., Inhibition of Pancreatic Cancer Growth by the Dietary Isoprenoids Farnesol and Geraniol, *Lipids*, vol. 32, No. 2, pp. 151–156 (1997).
Cox, et al., Analysis of Ras Protein Expression in Mammalian Cells, *Methods in Enzymology*, vol. 255, pp. 195–220 (1995).
Cox, et al., Farnesyltransferase inhibitors and cancer treatment: targeting simply Ras?, *Biochimica et Biophysica Acta*, vol. 1333, pp. F51–F71 (1997).
Cox, et al., Specific Isoprenoid Modification Is Required for Function of Normal, but Not Oncogenic, Ras Protein, *Mol. Cell. Biol.*, vol. 126, pp. 2606–2615 (1992).
Dawe, et al., Novel Modifications to the Farnesyl Moiety of the a–Factor Lipopeptide Pheromone from *Saccharomyces cerevisiae*: A Role for Isoprene Modifications in Ligand Presentation, *Biochemistry*, vol. 36, pp. 12036–12044 (1997).
Dolence, et al., A mechanism for posttranslational modifications of proteins by yeast protein farnesyltransferase, *Proc. Natl. Acad. Sci. USA*, vol. 92, pp. 5008–5011 (1995).

Finder, et al., Inhibition of Protein Geranylgeranylation Causes a Superinduction of Nitric–oxide Synthase–2 by Interleukin–1β in Vascular Smooth Muscle Cells, *J. Biol. Chem.*, vol. 272, No. 21, pp. 13484–13488 (1997).
Gibbs, et al., A Steroselective Palladium/Copper–Catalyzed route to isoprenoids: Synthesis and Biological Evaluation of 13–Methylidenefarnesyl Diphosphate. J. Org. Chem., vol. 60, No. 24, pp. 7821–7829 (1995).
Kohl, et al., Inhibition of farnesyltransferase induces regression of mammary and salivary carcinomas in ras transgenic mice, *Nature Med.*, vol. 1, No. 8, pp. 792–797 (1995).
Leonard, Ras Farnesyltransferase: A New Therapeutic Target, *J. Med. Chem.*, vol. 40, No. 19, pp. 2971–2990 (1997).
Lowy, et al., Rational cancer therapy, *Nature Med.*, 1:8, pp. 747–748 (1995).
McGuire, et al., Platelet–derived Growth Factor Receptor Tyrosine Phosphorylation Requires Protein Geranylgeranylation but not Farnesylation, *J. Biol. Chem.*, vol. 271, No. 44, pp. 27401–27407 (1996).
Mu, et al., Cuprate–Mediated Synthesis and Biological Evaluation of Cyclo–propyl– and tert–Butylfarnesyl Diphospate Analogs, *J. Org. Chem.*, vol. 61, pp. 8010–8015 (1996).
Roullet, et al., Farnesol Inhibits L–type $Ca^{2+}$ Channels in Vascular Smooth Muscle Cells, *J. Biol. Chem.*, vol. 272, No. 15, pp. 32240–32246 (1997).
Scholten, et al., Inhibitors of Farnesyl:Protein Transferase—A Possible Cancer Chemotherapeutic, *Bioorg. Med. Chem.*, vol. 4, No. 9, pp. 1537–1543 (1996).
Yokoyama, et al., Differential Prenyl Pyrophosphate Binding to Mammalian Protein Geranylgeranyltransferase–I and Protein Farnesyltransferase and Its Consequences on the Specifity of Protein Prenylation, *J. Biol. Chem.*, vol. 272, No. 7, pp. 3944–3952 (1997).

* cited by examiner

*Primary Examiner*—Taofiq Solola
(74) *Attorney, Agent, or Firm*—Rohm & Monsanto, PLC

(57) ABSTRACT

Farnesyl diphosphate analogs, specifically the 3-substituted alcohol precursors of the diphosphate analogs, 3-allylfarnesol and 3-vinylfarnesol, are potent inhibitors of mammalian protein fanesyltransferase (FTase). 3-allylgeranylgeraniol is a highly specific cellular inhibitor of protein geranylgeranylation (GGTase I). Furthermore, these compounds are able to efficiently block the anchorage-dependent growth of ras transformed cells. While 3-allylfarnesol inhibits protein farnesylation in situ, 3-vinylfarnesol instead leads to the abnormal prenylation of proteins with the 3-vinylfarnesyl group. In a similar manner, treatment with 3-allylgeranylgeraniol inhibits protein geranylgeranylation while 3-vinylgeranylgeraniol restores protein geranylgeranylation in cells.

12 Claims, 11 Drawing Sheets

A. H-Ras-F

B. H-Ras-GG

PRENYL TRANSFERASE INHIBITORS

CROSS-REFERENCE TO RELATED APPLICATIONS

This application claims the benefit of, and is a continuation-in-part patent application of, U.S. Provisional Application No. 60/089,625 filed on Jun. 16, 1998.

STATEMENT GOVERNMENT RIGHTS

This invention has been made with Government support under contract no. CA-67292 awarded by the National Institutes of Health. The government has certain rights in this invention.

BACKGROUND OF THE INVENTION

1. Field of the Invention

This invention relates generally to novel analogs of farnesol and geranylgeraniol, and more specifically to 3-substituted farnesol and geranylgeraniol analogs, that block the prenylation of proteins in cells.

2. Background of the Prior Art

Proteins are modified by a mevalonate pathway intermediate. There are three different protein prenylation motifs in this pathway—farnesylation, geranylgeranylation, and bis-geranylgeranylation. The first modification is carried out by an enzyme, protein farnesyl transferase (FTase), which recognizes the CAAX box (where A=aliphatic amino acid and X=Ser or Met) at the carboxyl terminus of the protein substrate and then attaches the farnesyl group from farnesyl diphosphate (FPP) to the free sulfhydryl of the cysteine residue. FIG. 1 is a reaction pathway for protein farnesylation of, illustratively, a Ras protein. The second, closely related enzyme, protein geranylgeranyltransferase I (GGTase I), attaches a geranylgeranyl moiety from geranylgeranyl diphosphate (GGPP) to a cysteine in a similar CAAX box, where leucine (X=Leu) is the carboxyl terminal residue. The third enzyme, GGTase II, attaches two geranylgeranyl residues to two cysteine residues at the carboxyl terminus of Rab proteins.

Once initial studies demonstrated that the key signal transduction protein and oncogene product Ras is farnesylated, FTase became the subject of intense research interest on the basis that inhibitors of this enzyme could block the action of mutant Ras proteins and halt the growth of ras-transformed cells, and therefore would be potential anti-cancer agents. Mutant forms of Ras proteins are involved in about 30% of human cancers. These include pancreatic adenocarcinomas, colon adenocarcinomas, and adenomas; thyroid carcinomas and adenomas; lung adenocarcinomas; myeloid leukemia; and melanomas. Therefore, there is a need in the art for an FTase inhibitor that can block the growth of ras-transformed cells in vivo.

Significant progress has been made in the development of peptide-based FTase inhibitors, and some of these compounds have shown great promise in vivo as potential anti-cancer agents. Merck has reported a peptidomimetic inhibitor that is effective in vivo in a mouse pancreatic carcinoma model. However, the peptide-based inhibitors are complicated molecules that require numerous synthetic steps to prepare. This limits their availability and increases cost. Moreover, the peptidomimetic inhibitors are not able to penetrate cell membranes due to their polarity. Therefore, in order to be administered in vivo, these drugs must be converted to a prodrug ester form. Even in the prodrug form, the in situ (cell culture) and in vivo potency is several orders of magnitude less than the potency of the parent inhibitor and the isolated enzyme. Furthermore, since peptide-based drugs are usually polar, they are susceptible to proteolytic degradation. This prevents the compound, even in its prodrug form, from being given orally, thereby necessitating dosing by i.v. administration.

While the specificity of FTase for its protein substrate has been extensively explored, there have only been limited reports on its specificity for farnesyl pyrophosphate or farnesyl diphosphate (FPP; Compound 10 on FIG. 1). FPP is a biosynthetic intermediate that occupies a key branch point in the mevalonate pathway. The primary route for FPP metabolism is its conversion into squalene by the enzyme squalene synthase. Squalene is then transformed by a series of enzymatic steps to cholesterol. Squalene synthase has attracted significant interest as a potential additional target for cholesterol-lowering agents. FPP is also converted in the cell to other important isoprenoids, such as dolichol and ubiquinone, which are utilized in protein glycosylation and electron transport, respectively. Most recently it has been recognized that FPP plays an additional crucial role in the cell. It is utilized by the enzyme protein farnesyl transferase (FTase) as the source of a farnesyl moiety that is attached to the cysteine sulfhydryl on the ras G proteins and certain other proteins which bear a carboxyl-terminal Cys—AAX—OH sequence. This farnesylation event and the subsequent proteolysis and carboxymethylation modifications serve to increase the hydrophobicity of these proteins, and thus, convert them to peripheral membrane proteins. There is, therefore, a need for FPP-based FTase inhibitors as probes for analyzing the FPP-binding site of FTase.

Novel FPP analogs were synthesized as probes of the FPP-binding site of FTase and characterized by their interaction with recombinant yeast FTase (yFTase). The vinyl analog, 3-vinyl farnesyl diphosphate (3-vFPP; FIG. 1, Compound 10a) was designed as a potential mechanism-based inhibitor, but instead was a poor alternative substrate for yFTase. These results were reported in Gibbs, et al., *J. Org. Chem.*, Vol. 60, pages 7821–7829 (1995). In contrast, a sterically encumbered analog, 3-tert-butyl farnesyl diphosphate (3-tbFPP; FIG. 1, Compound 10b), is an exceptionally poor substrate and a potent competitive inhibitor of this enzyme. See, Mu, et al., *J. Org. Chem.*, Vol. 61, pages 801–8015 (1996).

The results obtained by the various prenyl transferase inhibitors proposed in the art demonstrate unpredictability with respect to inhibition of FTase or geranylgeranylase (GGTase) in vitro and in vivo. There is, thus, a need for prenyl transferase inhibitors that are effective against mammalian FTase, which is the clinically relevant variant of the enzyme, both in vitro for research purposes and in vivo for therapeutic purposes.

It is, therefore, an object of this invention to provide novel prenyl transferase inhibitors that are easier to prepare than other farnesyl analog FTase inhibitors.

It is also an object of this invention to provide novel prenyl transferase inhibitors that exhibit better cellular penetration.

It is another object of this invention to provide novel prenyl transferase inhibitors that are useful as anticancer agents.

It is a still further object of this invention to provide novel prenyl transferase inhibitors that are bioavailable and non-toxic to the host and that are cytotoxic as compared to other FTase inhibitors that are merely cytostatic.

It is yet another object of this invention to provide novel geranylgeranyl transferase inhibitors that are potentially useful as restenosis inhibitors.

SUMMARY OF THE INVENTION

The foregoing and other objects are achieved by this invention which comprises, in a composition of matter embodiment, 3-substituted isoprenol analogs that block the prenylation of proteins in cells. In preferred embodiments, the isoprenol analogs are analogs of the alcohols, farnesol and geranylgeraniol, as well as their diphosphate derivatives. The active, diphosphate derivatives of these compounds are potent inhibitors of mammalian protein prenyltransferases. The alcohol precursors efficiently block the growth of anchorage-independent ras-transformed cells.

The farnesol and geranylgeraniol analogs within the contemplation of this invention, include without limitation, Formula (I):

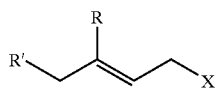

wherein R' is a $C_{10}$–$C_{20}$ saturated or unsaturated alkyl, aryl, heteroaryl, or cycloalkyl which, in some embodiments, include substituents, some of which may contain heteroatoms, such as N, O, S, and F; R is a $C_2$–$C_{10}$ saturated or unsaturated alkyl, aryl, cycloalkyl, or $C_6$–$C_{10}$ aromatic or heteroaromatic group which may be substituted; and X is —OH or —$P_2O_7$. As used herein, the composition includes enantiomers, stereoisomers, and geometric isomers.

In preferred embodiments, R' is geranyl and farnesyl and R is selected from the group vinyl, ethyl, allyl, saturated and unsaturated isomers of propyl, butyl, and pentyl, cyclopropyl, isobutyl, cyclopentyl, phenyl and heterosubstituted moieties, such as fluorophenyl, (trimethylsilyl)methyl, 1-ethoxyvinyl, and 2-furanyl, 2-thiophenyl.

In a preferred embodiment, the 3-substituted farnesol or geranylgeraniol analogs have of the following formulae (II) and (III):

Formula(II):

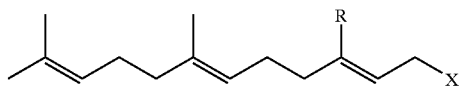

Formula(III):

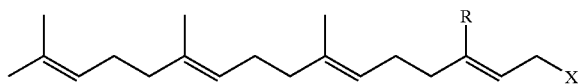

wherein R is preferably vinyl, allyl, isopropyl, cyclopropyl, isobutyl, cyclopentyl, or phenyl. However, R may comprises other substituted or unsubstituted $C_2$–$C_{10}$ saturated and unsaturated alkyl, aryl, and cycloalkyl groups, $C_6$–$C_{10}$ aromatic groups, and heteroaromatic groups, some of which are illustratively shown in FIG. 2B. As stated above, the isoprenyl alcohols are prodrugs for the active diphosphate form where R is methyl.

Illustrative embodiments of the 3-substituted farnesol and geranylgeraniol analogs are shown on FIGS. 2A and 2B. The compounds are identified on FIGS. 2A and 2B by their common name. Those compounds that are specifically referenced in this application are identified by compound number, and if abbreviated herein, the abbreviation.

In particularly preferred embodiments, the 3-substituted compounds are 3-vinyl farnesol, 3-allylfarnesol, 3-isopropylfarnesol, 3-vinyl geranylgeraniol, 3-allylgeranylgeraniol, and 3-isopropylgeranylgeraniol. In the studies reported herein, 3-allylfarnesol inhibits protein farnesylation in situ and 3-vinylfarnesol instead leads to the abnormal prenylation of proteins with the 3-vinylfarnesyl group. In a similar manner, treatment with 3-allylgeranylgeraniol inhibits protein geranylgeranylation while 3-vinylgeranylgeraniol restores protein geranylgeranylation in cells. Furthermore, 3-allylgeranylgeraniol is one of the most potent inhibitors of GGTase I discovered to date. Studies have now confirmed that the 3-allyl and 3-vinyl analogs are potently cytostatic and cytotoxic to human pancreatic cancer cells (HPAC) in situ. In addition, the 3-allyl analogs have been shown to exhibit selective cytostatic effects on a mouse colon 38 tumor cell line at levels where the same amount has no effect on human fibroblasts. Moreover, preliminary animal studies with severe combined immunodeficiency (SCID) mice indicate that these compounds are non-toxic.

As indicated above, the isoprenol derivatives, 3-substituted farnesol or geranylgeraniol, are precursors, or prodrugs, and as such, rely on the target cells to carry out the biological activation. Therefore, the isoprenol derivative are administered as an anticancer agent, specifically as a prodrug for the active diphosphate, to inhibit the respective prenyl transferases in cells. In particular, inhibition of FTase reduces the level of protein farnesylation in a host, and hence reduces the activity of proteins, such as Ras proteins, which require farnesylation for activation. Of course, these compounds can exert a multitude of other beneficial effects, both known and yet to be discovered.

In a method of use embodiment, a method of treating cancer, specifically cancers of the type which are susceptible to treatment by prenyl transferase inhibitors, comprises administering an effective amount of at least one 3-substituted isoprenol derivative. In particularly preferred embodiments, the 3-substituted isoprenol derivative is selected from the group consisting of 3-allyl farnesol, 3-vinyl farnesol, 3-allyl geranylgeraniol, and 3-vinyl geranylgeraniol. These cancers include any cancer having tumors which are associated with abnormal activity of oncogenes in the ras family, including the three mammalian ras genes, H-ras, K-ras, and N-ras. Other ras proteins include those whose DNA coding regions hybridize to the coding regions of known ras genes. Abnormal ras activity is associated with 30–50% of all lung and colorectal carcinomas and up to 95% of pancreatic carcinomas. Of course, the type of cancers susceptible to prenyl transferase inhibitors is not limited to those bearing ras mutations. Protein prenylation is required for the activity of several signal transduction pathways. Thus, the 3-substituted isoprenol derivatives of the present invention may be used to treat cancers bearing mutations in other oncogenes, including but not limited to various growth factor receptor genes, rho genes, and PTP-CAAX genes. Other farnesyl transferase inhibitors have proven to be effective at blocking the growth of cancer cells that do not bear a ras mutation, as well as those that do. See, Cox, et al., *Biochim. Biophys, Acta*, Vol. 1333, pages F51–F71 (1997).

The novel analogs may be administered alone or in conjunction with other drugs. The analogs may be administered in a variety of ways, orally, parenterally, topically, etc. In injectable forms, the analogs may be delivered subcutaneously, intraperitonealy, or intravascularly. Of course, the analogs may be combined with a delivery vehicle and other fillers, excipients, and the like, as are known in the art to form a pharmaceutical dosage form. Illustrative dosage forms include, tablets, capsules, gels, suspensions, emulsions, liposomes, nanoparticles, etc. Oral dosage forms may be encapsulated or coated, as necessary, in any manner which is known in the art, to protect and/or release the active agent at the appropriate point in the gastrointestinal system.

It has been reported that inhibition of protein geranylgeranylation causes superinduction of nitric oxide synthase (NOS-2) by interleukin-1β in vascular smooth muscle cells and hepatocytes. Finder, et al., *J. Biol. Chem.*, Vol. 272, No. 21, pages 13484–13488 (1997). This indicates that the 3-substituted geranylgeraniol analogs may inhibit restenosis following angioplasty or other surgical intervention, such as catheterization. It is therefore, contemplated within the invention, that the 3-substituted geranylgeraniol derivatives may be administered to a mammal to inhibit restenosis.

It has also been reported that farnesol inhibits $Ca^{+2}$ signals in arteries and vascular smooth muscle cells and possesses $Ca^{+2}$ channel blocker properties. Roulle, et al., *J. Biol. Chem.*, Vol. 272, pages 32240–32246, Dec. 19, 1997. Therefore, it is also contemplated that the novel 3-substituted isoprenol derivatives disclosed herein may be administered to a mammal for their vasoactive properties.

BRIEF DESCRIPTION OF THE DRAWING

Comprehension of the invention is facilitated by reading the following detailed description, in conjunction with the annexed drawing, in which.

DETAILED DESCRIPTION

Illustrative methods of making the 3-substituted isoprenoid analogs of the present invention are set forth hereinbelow:

Stereoselective Synthesis of Farnesyl and Geranylgeranyl Analogs

A stereoselective route to the 3-substituted farnesyl or geranylgeranyl analogs is illustrated by the production of 13-methylidenefarnesyl diphosphate, or 3-vinylfarnesyl diphosphate (3-vFPP; Compound 19) which is the active form of the desired alcohol precursor 3-vinyl farnesol (Compound 17). The synthetic sequence, shown in FIG. 3A, includes the stereoselective Pd(0)/Cu(I)-catalyzed coupling of a vinyl triflate with an organostannane reagent, vinyltributyltin, to obtain the desired Z isomer of the divinyl ester. The divinyl ester is reduced to the corresponding alcohol. The alcohol is diphosphorylated, illustratively through a synthetic route from the alcohol into an allylic chloride which is treated with tris(tetrabutylammonium) hydrogen diphosphate to yield the desired diphosphate.

By using a polar aprotic solvent, illustratively dimethyl formamide (DMF), instead of THF, in the synthesis of the triflate (Compound 15) from the β-ketoester (Compound 14), the opposite geometric isomer of the triflate, and consequently the alcohol and the diphosphate, is obtained.

Figure 2A:
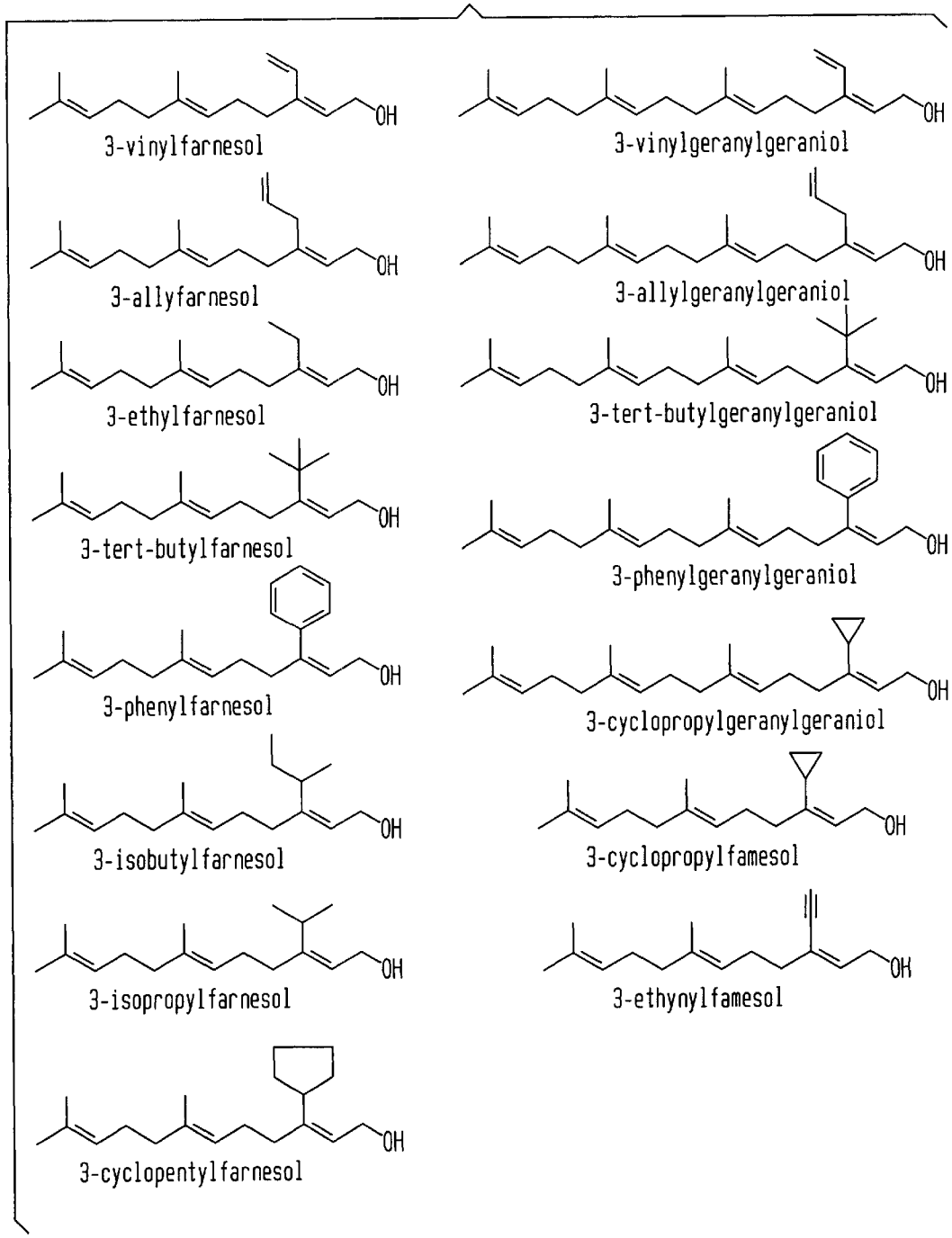
FIGS. 2A and 2B illustrate chemical formulae of illustrative 3-substituted farnesol and geranylgeraniol analogs in accordance with the present invention.
Figure 2B:
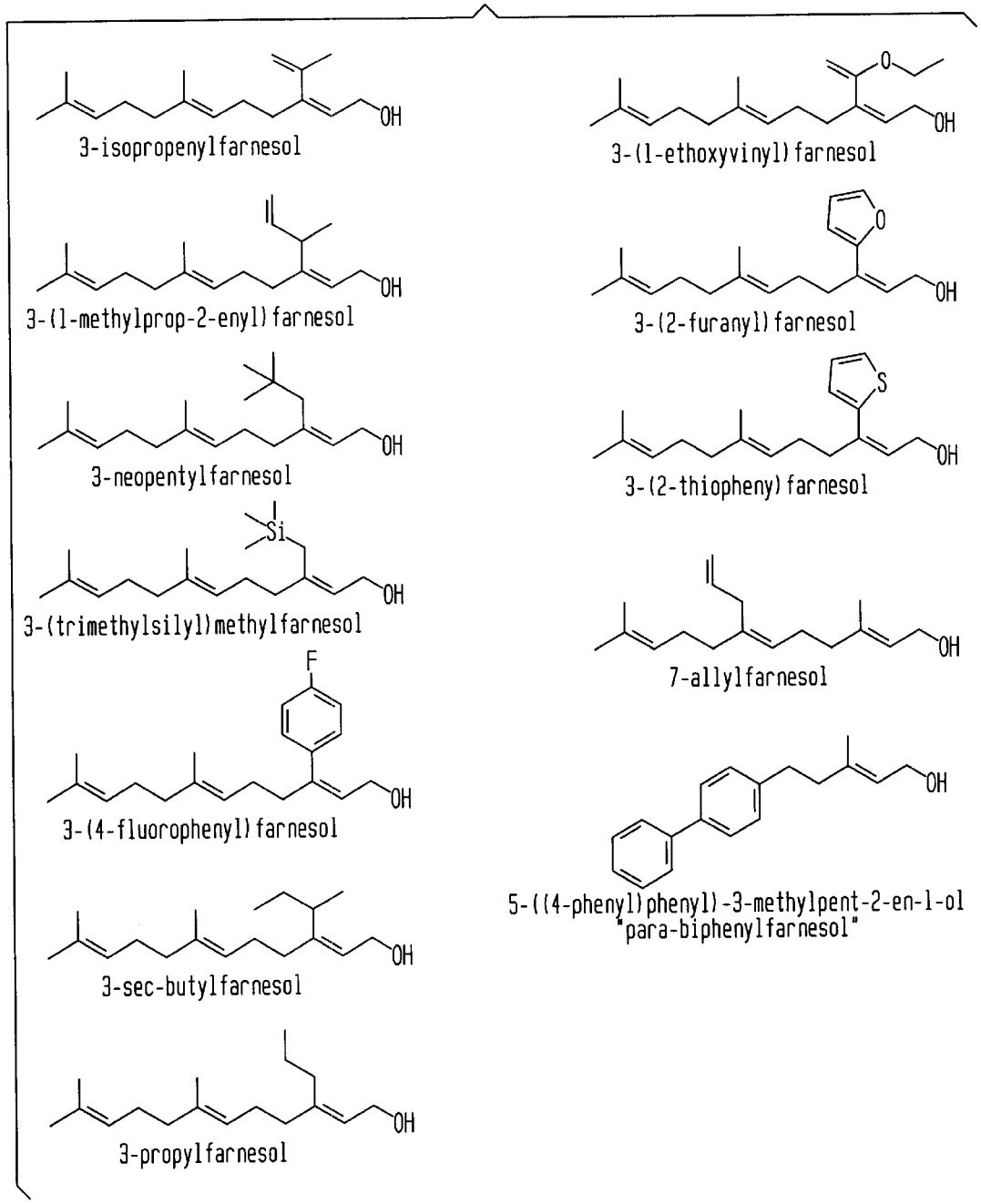

The general methods disclosed herein can be adapted by those of skill in the art to produce a multitude of compounds, including the stereoselective production of a broad range of substituted allylic alcohols. By selecting the appropriate starting compounds, farnesols and geranylgeraniols substituted at positions other than 3-, can be synthesized. Illustrative examples, are 7-allylfarnesol and para-biphenylfarnesol shown on FIG. 2B.

The 3-ethyl and 3-phenyl farnesol analogs were produced by the same procedure using the appropriate organostannane. The 3-tert-butyl and 3-cyclopropyl farnesyl and geranylgeranyl analogs were synthesized using a cuprate coupling procedure, which is illustrated herein by the method of producing 3-tert-butyl farnesol.

As illustrated below, by the methods of making 3-vinyl geranylgeraniol and 3-allyl geranylgeraniol, the geranylgeranyl analogs may be produced in a similar manner starting with the appropriate triflate.

Figure 3A:
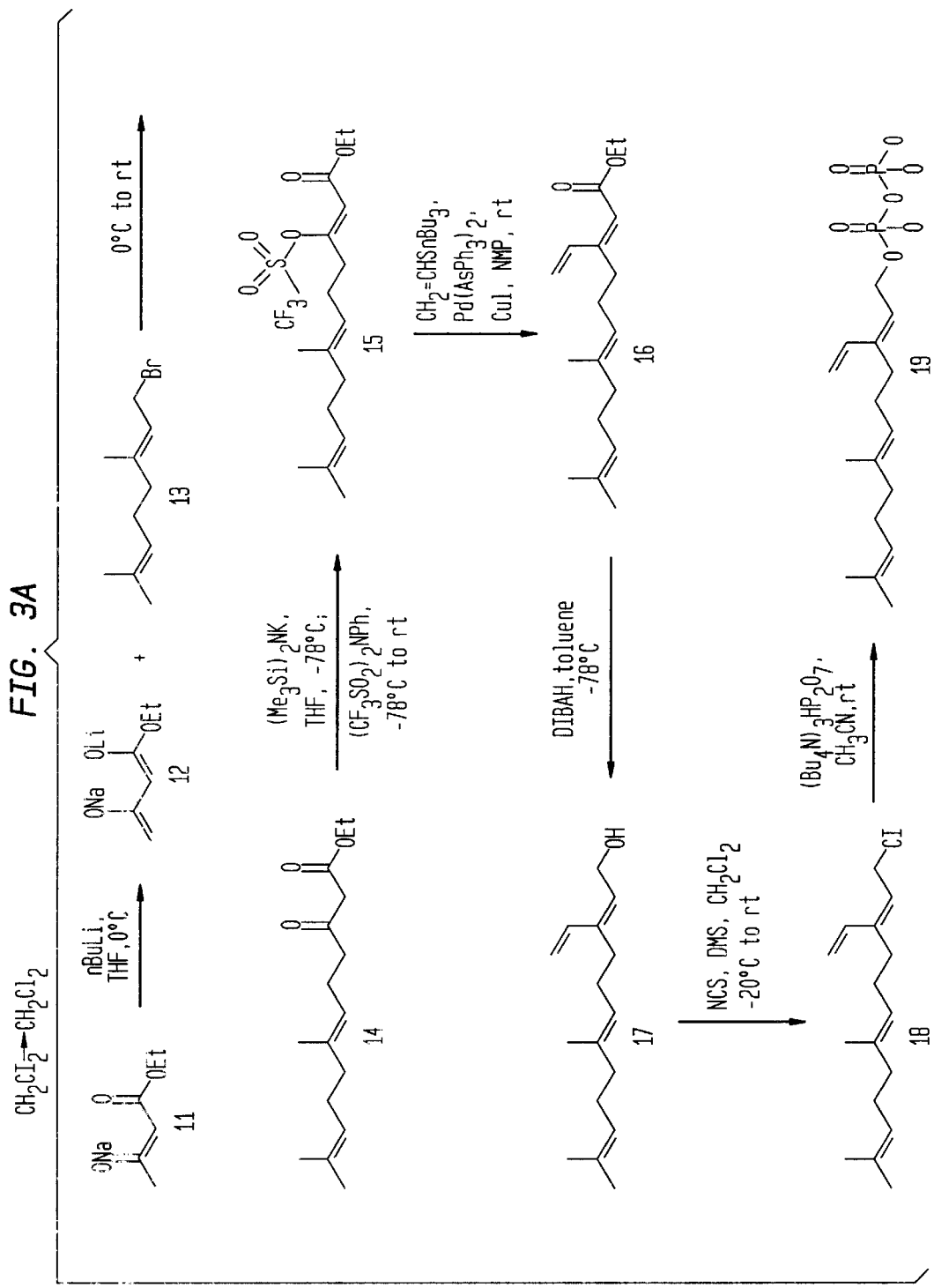
FIG. 3A is a synthetic pathway for producing a 3-substituted isoprenyl diphosphate, illustratively 3-vinylfarnesyl diphosphate (3-vFPP)

I. 3-Substituted Farnesyl Analogs a. Vinyl Analogs:

Referring to FIG. 3A, the detailed procedures for making 3-vinyl farnesol and 3-vinyl farnesyl diphosphate (3-vFPP) are set forth below:

Ethyl 7,11-Dimethyl-3-oxododeca-6,10-dienoate (Compound 14)

The sodium salt of ethyl acetoacetate (Compound 11; 20.0 mmol, 3.04 g) was dissolved in 40 ml of tetra hydrofuran (THF) (distilled from sodium/benzophenone ketyl) and cooled to 0° C. n-Butyllithium (2.0 M in cyclohexane, 21.0 mmol, 10.6 ml) was added dropwise to the cooled solution to form a solution of the dianion Compound 12. After 20 minutes, geranyl bromide (Compound 13; 10.0 mmol, 1.98 ml, 2.16 g) was added to the solution of dianion and stirring was continued for an additional 30 minutes at 0° C. The reaction mixture was poured into a cold saturated solution of potassium hydrogen phosphate and extracted with ether (3×20 ml). The combined organic layers were washed with water (20 ml), dried over $MgSO_4$, filtered, and concentrated. Flash chromatography (9:1 hexane/ethyl acetate) afforded 2.05 g (77% yield) of Compound 14 as an oil.

Ethyl 3-(((Trifluoromethyl)sulfonyl)oxy)-7,11-dimethyldodeca-2(Z),6(E),10-trienoate (Compound 15)

A solution of the β-keto ester Compound 14 (4.0 mmol, 1.064 g) in THF (10 ml; distilled from sodium/benzophenone ketyl) was added to potassium bis (trimethylsilyl)amide (0.5 M in toluene, 4.8 mmol, 9.6 ml)

at −78° C. N,N,-bis(Trifluoromethanesulfonyl-N-phenylamine (4.8 mmol, 1.72 g) was added and the mixture was allowed to warm to room temperature overnight. The mixture was taken up in 30 ml of ether and washed with a 10% citric acid solution (2×20 ml) and water (1×20 ml). The ether layer was dried over $MgSO_4$, and the solvent removed in vacuo. Purification by flash chromatography (95:5 hexane/ethyl acetate) gave 0.845 g (53% yield) of the vinyl triflate, Compound 15, as an oil.

Ethyl-3-Vinyl-7,11-dimethyldodeca-2(Z),6(E), (Compound 16) 10-Trienoate and its Isomer Ethyl-3-vinyl-7,11-dimethyldodcea-2(E),6(E),10-trienoate Triflate Compound 15 (1.09 mmol, 434 mg), triphenyl arsine ($Ph_3As$; 0.11 mmol, 34 mg), bis(benzonitrile) palladium (II) chloride (0.054 mmol, 21 mg), and CuI (0.11 mmol, 21 mg) were placed in an argon-flushed flask and dissolved in NMP (1.1 ml). Vinyltributyltin (1.3 mmol, 412 mg, 0.38 ml) was then added, and the reaction mixture was stirred for about 15 hrs at room temperature. The mixture was then dissolved in 1:1 EtOAc/hexanes (100 ml), washed with aqueous KF (2×30 ml) and water (20 ml), dried over $MgSO_4$, and then filtered and concentrated. Purification by flash chromatography (98:2 hexane/EtOAc) afforded the desired vinyl ester (234 mg; 78% yield). The ratio of E isomer to Z (Compound 16) isomer was determined to be 94:6 by integration of the NMR peaks at $\partial 7.74$ and 6.332.

3-Vinyl-7,11-dimethyldodeca-2(Z),6(E),10-trien-1-ol (Compound 17)

A solution of the vinyl ester Compound 16 (0.85 mmol, 234 mg) in toluene (4.2 ml; HPLC grade dried over 4 Å sieves) was treated at −78° C. under argon with diisobutylaluminum hydride (DIBAH; 1.0 M in toluene; 2.38 mmol, 2.38 ml). After the addition of the hydride, the mixture was stirred for 1 hour at −78° C. The reaction was quenched by adding the reaction mixture to saturated aqueous potassium sodium tartrate (40 ml). The organic phase was separated, and the aqueous phase was extracted with ethyl acetate (3×30 ml). The combined organic layers were washed with water (20 ml) and brine (20 ml) and dried ($MgSO_4$). Filtration and concentration followed by flash chromatography (9:1 hexane/ethyl acetate) gave 173 mg (86%) of vinyl alcohol, 3-vinyl farnesol (Compound 17).

1-Chloro-3-vinyl-7,11-dimethyldodeca-2(Z),6(E),10-triene (Compound 18)

N-Chlorosuccinimide (NCS; 0.42 mmol, 60 mg) was dissolved in 1.75 ml of methylene chloride ($CH_2Cl_2$, distilled from $CaH_2$). The resulting solution was cooled to −30° C. in a dry ice/acetonitrile bath. Dimethyl sulfide (DMS; 0.45 mmol, 0.03 ml, 27 mg) was added dropwise by a syringe, and the mixture was warmed to 0° C., maintained at that temperature for 5 minutes, and then cooled to −40° C. The resulting milky white suspension was added dropwise to a solution of the vinyl alcohol Compound 17 (0.38 mmol, 90 mg) in 5 ml of distilled $CH_2Cl_2$. The suspension was warmed to 0° C. and stirred for 2 hours. The ice bath was removed and the reaction mixture was allowed to warm to room temperature and stirred for an additional 15 minutes. The resulting solution was washed with hexane (2×20 ml). The hexane layers were then washed with brine (2×10 ml) and dried over of $MgSO_4$. Concentration afforded 74 mg (77% yield) of the vinyl chloride Compound 18 as an oily liquid which was used directly in the next step without purification.

3-Vinyl-7,11-dimethyldodeca-2(Z),6(E),10-triene 1-Diphosphate (13-Methylidenefarnesyl Diphosphate) (3-vFPP; Compound 19)

Figure 3B:
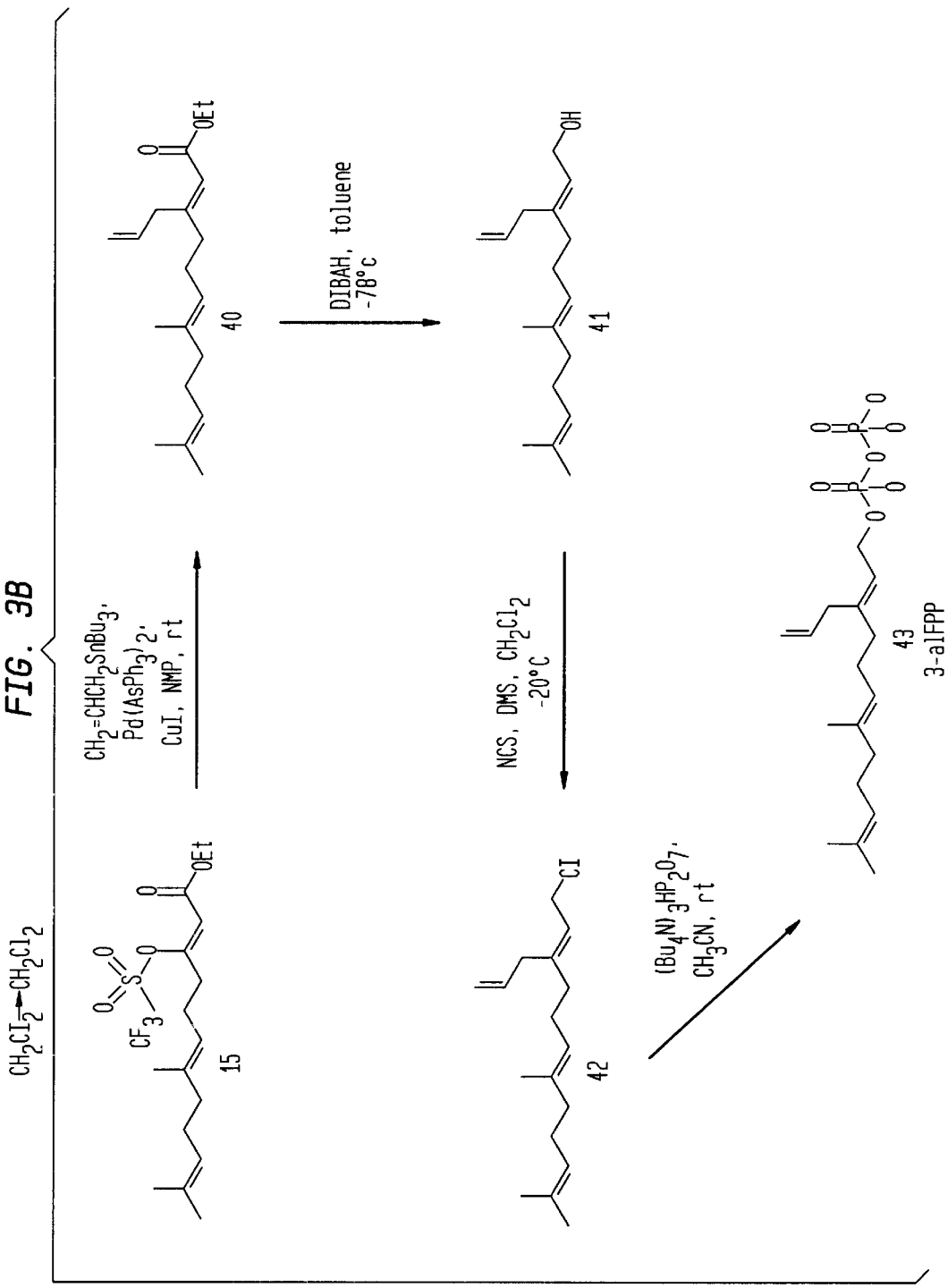
FIG. 3B is a synthetic pathway for producing a 3-allylfarnesyl diphosphate.

Tris (tetrabutylammonium) hydrogen pyrophosphate (0.40 mmol, 365 mg) was dissolved in acetonitrile (3 ml; freshly distilled from $P_2O_5$) under an argon atmosphere. Vinyl chloride Compound 18 (0.10 mmol, 25 mg) was added to the resulting milky white suspension. The mixture was stirred at room temperature for 2.5 hours, and the solvent was removed in a rotary evaporator at room temperature. The residue was dissolved in deionized water, and the resulting solution was passed through a 2×8 cm Dowex AG50 x 8 ion exchange column ($NH_4^+$form). The eluant was then concentrated in vacuo to yield a pale yellow solid which was then dissolved in 2 ml of 25 mM ammonium bicarbonate. The resulting mixture was purified by reverse-phase HPLC using a program of 5 minutes of 100% A followed by a linear gradient of 100% A to 100% B over 30 minutes wherein A is 25 mM aq. $NH_4HCO_3$ (pH 8.0) and B is $CH_3CN$; column, WatersµBondapak $C_{18}$ 25 mm×100 mm Radial-Pak cartridge; flow rate, 5 ml; UV monitoring at 214 and 230 nm. The retention time of the diphosphate Compound 19 was 25 minutes. The fractions containing the product were pooled, the acetonitrile was removed by rotary evaporation resulting in pure Compound 19 as a white, fluffy solid (88% yield).

b. Allyl Analogs:

Referring to FIG. 3B, certain details of the procedures for making 3-allyl farnesol and 3-allyl farnesyl diphosphate (3-alFPP) are set forth below:

Ethyl 3-Allyl-7,11-dimethyldodeca-2(Z),6(E),10-trienoate (Compound 40)

Ethyl 3-(((trifluoromethyl)sulfonyl)oxy)-7,11-dimethyldodeca-2(Z),6(E),10-trienoate (Compound 15; 317 mg; 0.79 mmol); triphenylarsine (25 mg; 0.82 mmol), bis(benzonitrile)palladium (II) chloride (15.3 mg; 0.39 mmol); and copper iodide (15.3 mg; 0.085 mmol) were placed in an argon-flushed flask and dissolved in 1.0 ml N-methylpyrrolidone (NMP). Once dissolved, allyltributyltin (534 mg; 0.5 ml; 1.61 mmol) was added dropwise and the reaction mixture was stirred for about 24 hours at 100° C. The mixture was then taken up in a 1:1 solution of hexanes/EtOAc (100 ml), washed with a 10% KF solution (2×30 ml) and water (20 ml), and then dried over $MgSO_4$, filtered and concentrated. Purification by flash chromatography using a 98:2 hexanes/EtOAc solvent system yielded 73 mg (31% yield) of the desired allyl ester, ethyl 3-allyl-7,11-dimethyldodeca-2(Z),6(E),10-trienoate.

3-Allyl 7,11-dimethyldodeca-2(Z),6(E),10-trien-1-ol (Compound 41)

A solution of the allyl ester, ethyl 3-allyl-7,11-dimethyldodeca-2(Z),6(E),10-trienoate (100 mg; 0.343 mmol), in 2.4 toluene was cooled to −78° C. under an argon atmosphere. Diisobutylaluminum hydride (1.0 M in toluene; 1.5 ml; 9.04 mmol) was then added and the reaction mixture was stirred at −78° C. for one hour. The reaction was quenched by adding the solution to saturated aqueous potassium sodium tartrate 930 ml. The organic phase was separated and the aqueous layer was extracted with ethyl acetate (3×20 ml). The organic layers were combined, washed with water (10 ml) and NaCl (10 ml) and dried over $MgSO_4$, filtered, and concentrated. Purification by flash chromatography using a 9:1 hexanes/EtOAc solvent system gave 68 mg (75.8% yield) of the desired allyl alcohol (3-allylfarnesol; Compound 41) as an oil.

1-Chloro-3-allyl-7,11-dimethyldodeca-2(Z),6(E),10-triene (Compound 42)

NCS (60mg; 0.42 mmol) was dissolved in 1.75 ml of $CH_2Cl_2$ and the resulting solution was cooled to −30° C. Dimethyl sulfide (27 mg; 0.03 ml; 0.45 mmol) was then added dropwise and the mixture was warmed to 0° C. and maintained at that temperature for 5 min then taken back down to −40° C. The allyl alcohol (68 mg; 0.261 mmol) dissolved in 5 ml $CH_2Cl_2$ was added dropwise to the resulting mixture. The suspension was again warmed to 0° C. and stirred for 2 hrs. The ice bath was removed, and the reaction mixture was allowed to warm to room temperature. At room temperature, the mixture was stirred for an additional 15 minutes. The mixture was washed with hexanes (2×15 ml) and the hexane layers were washed with brine (2×10 ml), dried over $MgSO_4$, filtered, and concentrated via a rotary evaporator to give 24 mg (33% yield) of the desired allyl chloride as an oil. Purification was not necessary for use in the next step.

3-Allyl-7,11-dimethyldodeca-2(Z),6(E),10-triene 1-diphosphate (Compound 43)

Figure 1:
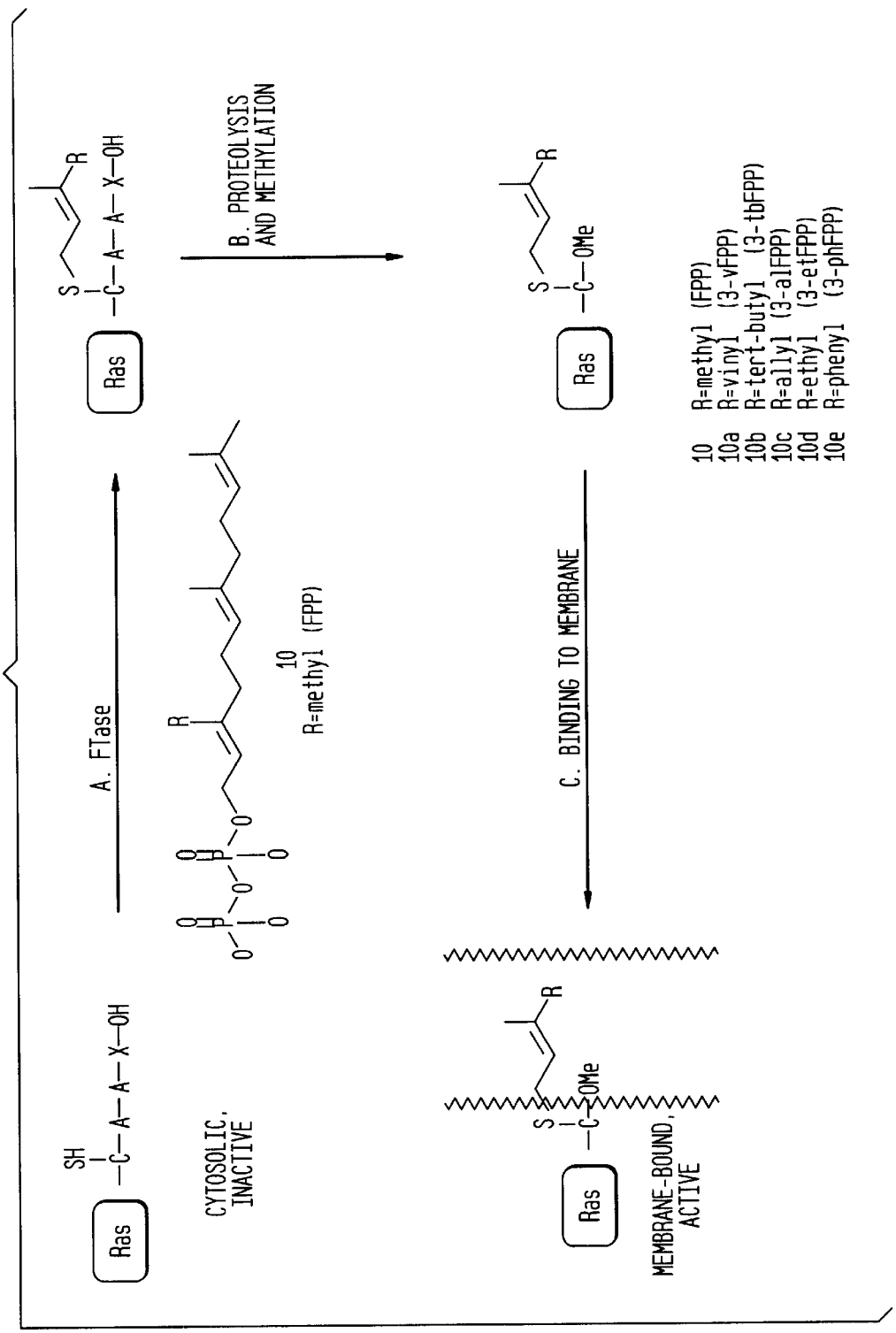
FIG. 1 is a reaction pathway for protein farnesylation of a Ras protein.

Tris(tetrabutylammonium)hydrogen pyrophosphate (365 mg; 0.40 mmol) was dissolved in 3 ml acetonitrile under an argon atmosphere. The allyl chloride (24 mg;0.086 mmol) was then added and the reaction was allowed to stir at room temperature for 2.5 hrs. The solvent was then removed via rota-vapping and the residue was dissolved in deionized water and passed through a 2×8 cm Dowex AG50x8 ion exchange column ($NH_4^+$ form). The eluant was concentrated by lyophilization and was immediately dissolved in 2 ml of a 25 mM ammonium bicarbonate solution. This mixture was purified by reverse-phase HPLC using a program of 5 min of 100% A followed by a linear gradient of 100% A to 100% B over a period of 30 min.(A is 25 mM ammonium bicarbonate (pH 8.0); B is $CH_3CN$; column was Waters μBondapak 25 mm×100 mm Radial-Pak cartridge; flow rate, 3 ml; UV monitoring at 214 nm and 230 nm). The fractions containing the product (retention time was 17 min.) were collected and the acetonitrile was removed by rotary evaporation at room temperature. The aqueous layer was lyophilized to give the 3-allylFPP (Compound 43; see also FIG. 1, Compound 1c; 31.5 mg; 90% yield) as a pure white solid.

c. tert-Butyl Analogs

Figure 4:
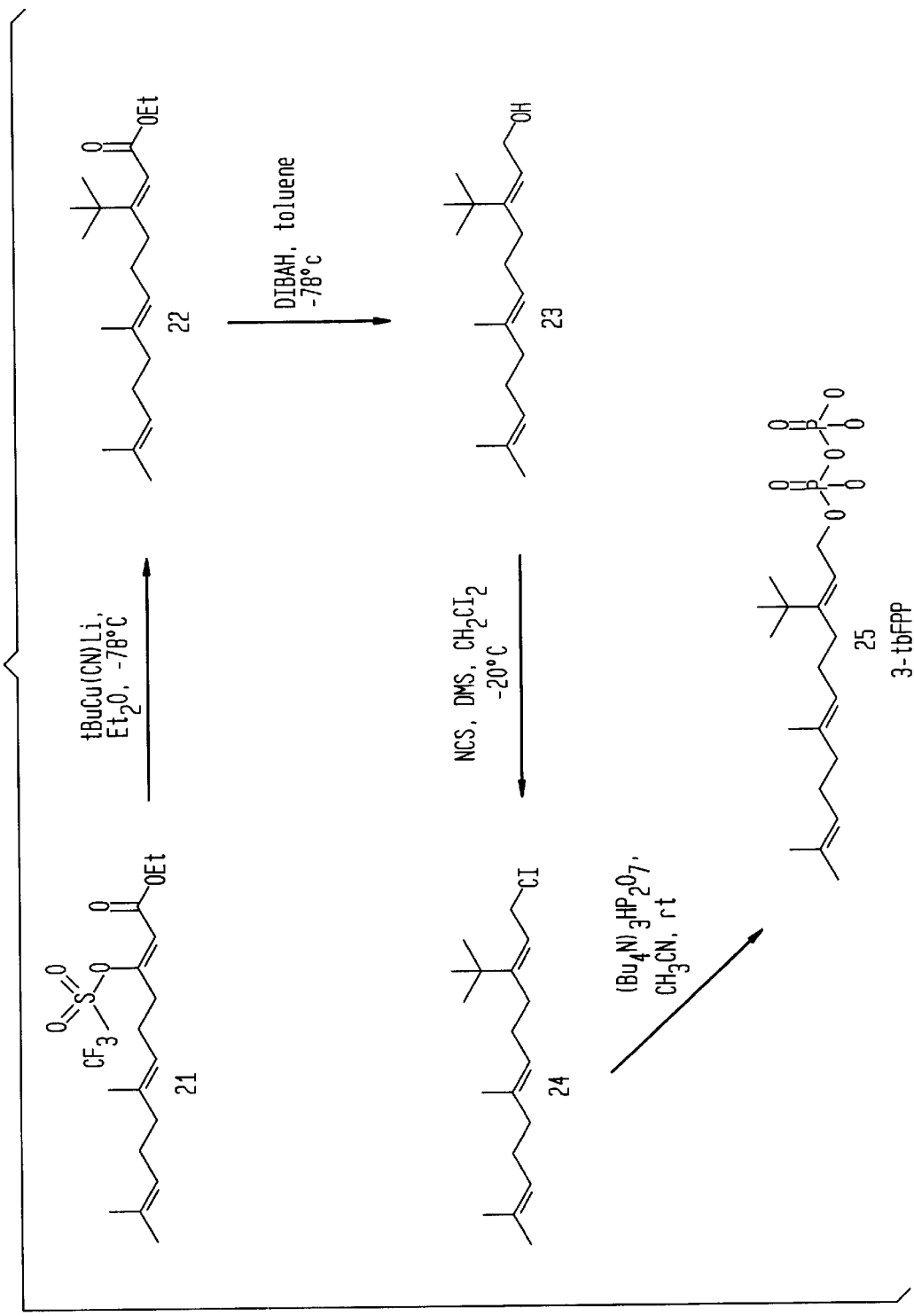
FIG. 4 is a cuprate-mediated synthetic pathway for producing 3-tert-butylfarnesyl diphosphate.

FIG. 4 illustrates a cuprate-mediated synthesis of 3-tert-butylfarnesyl diphosphate (3-tbFPP; Compound 25)

Ethyl 3-tert-Butyl-7,11-dimethyldodeca-2(Z),6(E),10-trienoate (Compound 22)

CuCN (0.47 mmol, 42 mg) and 1.0 ml of ether (distilled from Na/benzophenone) were placed in a flame-dried argon-flushed flask to form a slurry. The resulting slurry was cooled to −78° C. and then tert-butyllithium (1.7 M in pentane, 0.47 mmol, 0.28 ml) was added dropwise. The mixture was allowed to warm to 0° C. and then re-cooled to −78° C. A solution of the triflate, Compound 21 (0.32 mmol, 129 mg), in 1.0 ml of ether was added dropwise and the reaction mixture was stirred for 1 hour at −78° C. The mixture was warmed to 0° C. and quenched with 2 ml of saturated $NH_4Cl$. The organic layer was separated and the aqueous layer was extracted with ether (3×15 ml). The combined organic layers were dried over $MgSO_4$ and concentrated in vacuo. Flash chromatography (20: 1 hexanes/ethyl acetate) yielded Compound 22 as a colorless oil (67 mg, 68% yield).

Compound 22 can be produced in 91% yield by substituting tert-butylmagnesium chloride for tert-butyllithium in this procedure. This alternative method can be used successfully for the preparation of a variety of other 3-substituted isoprenoid esters, and consequently, for the preparation of corresponding 3-substituted isoprenoid alcohols.

3-tert-Butyl-7,11-dimethyldodeca-2(Z),6(E),10-trien-1-ol (Compound 23)

Ester Compound 22 (0.14 mmol, 42 mg) was treated with DIBAH (0.1 M in toluene, 0.35 mmol, 0.35 ml) at −78° C. under argon for 1 hour. Work-up and purification, as described above with respect to the 3-vinyl farnesol, afforded 33 mg (89% yield) of Compound 23, 3-tert-butyl farnesol, as a colorless oil.

In all of the synthetic routes proposed herein for producing the active, prenyl diphosphate analogs related to the 3-substituted prenyl alcohol derivatives, the alcohol is converted to the corresponding chloride and then to the corresponding diphosphate. Referring to FIG. 4, for example, the alcohol, 3-tert-butyl farnesol is converted to 3-tert-butyl-2(Z),6(E),10-trien-1-chloride (Compound 24) according to the following general procedure for the preparation of chlorides. The chloride is converted to the diphosphate, 3-tert-butyl-2(Z),6(E),10-triene diphosphate (3-tbFPP; Compound 25). The general procedure for converting the chloride to the diphosphate follows.

General Procedure for Preparation of Chlorides

In a flame-dried, round-bottomed flask were placed with N-chlorosuccinimide (1.2 equivalents) and dichloromethane (distilled from $CaH_2$). The solution was cooled to −30° C. in an acetonitrile/dry ice bath. Dimethyl sulfide (1.5 equivalents) was added dropwise to the cold solution, and the resulting milky white mixture was warmed to 0° C. for 5 minutes and re-cooled to −30° C. A solution of 1 equivalent of the alcohol in 1 ml of dichloromethane was added dropwise to the mixture at −30° C. The reaction was slowly warmed up to 0° C. and stirred for an additional hour at that temperature. The resulting clear, colorless solution was stirred at room temperature for 20 minutes and poured into 10 ml of cold brine solution. The aqueous layer was extracted with 2×15 ml hexanes, and the combined organic layers were washed with 10 ml of cold brine solution and dried over $MgSO_4$. Concentration (rotary evaporation followed by high vacuum at room temperature) afforded the chlorides as colorless or pale yellow oils which were used directly for the next reaction.

General Procedure for Preparation of Diphosphates

In a flame-dried, round-bottom flask were placed two equivalents of Tris(tetra-n-butylammonium)hydrogen pyrophosphate and 1.0 ml of acetonitrile (distilled from $P_2O_5$). The mixture was cooled to 0° C. and 1 equivalent of chloride in 0.5 ml of acetonitrile was added dropwise. The reaction was allowed to stir at room temperature for two hours, and the solvent was removed by rotary evaporation at room temperature. The residue was dissolved in 1–2 ml of ion exchange buffer (1:49 v/v isopropyl alcohol and 25 mM $NH_4HCO_3$) and was passed through a column containing 3–10 ml cation-exchange resin (Dowex AG 50W-X8, $NH_4^+$ Form). The column was eluted with two column volumes of ion exchange buffer at a flow rat of 1 ml/min. The eluant was dried by lyophilization and a pale yellow solid was obtained. The crude product was dissolved in 1–3 ml of 25 mM $NH_4HCO_3$ and purified by reverse-phase HPLC using a program of 5 mm of 100% A followed by a linear gradient of 100% A to 100% B over 30 min. (A: 25 mM aqueous NH$_4$HCO$_3$, pH 8.0; B: CH$_3$CN; Vydac pH-stable C$_8$ 4.6 mm×250 mm column flow rate: 1.0 ml UV monitoring at 214 and 254 μm). The fractions were collected, pooled and dried by lyophilization, and the diphosphates were obtained as white fluffy solids.

d. Cyclopropyl Analogs:

Ethyl 3-Cyclopropyl-7,11-dimethyldodeca-2(Z),6 (E),10-trienoate

To a solution of cyclopropyl bromide (0.38 mmol, 31 μl) in 1.0 ml ether was added tert-butyllithium (1.7 M in pentane, 0.77 mmol, 0.45 ml) under argon at −78° C. The resulting solution was stirred for 15 minutes. Triflate (Compound 21; 0.26 mmol, 102 mg) in 1 ml ether was added to the mixture at that temperature with stirring for 1.5 hours. Workup and purification as described above afforded 53 mg (71% yield) of β-keto ester as a colorless oil.

3-Cyclopropyl-7,11-dimethyldodeca-2(Z),6(E),10-trien-1-ol

To a solution of the β-keto ester produced in the preceding step (0.22 mmol, 6 mg) in 1.0 ml of toluene (HPLC grade, stored over 4 Å sieves) was added DIBAH (1.0 M in toluene, 0.54 mmol, 0.54 ml) at −78° C. under argon. After being stirred for 1 hour at this temperature, the reaction was quenched with saturated sodium potassium tartrate (20 ml). The organic layer was separated, and the aqueous phase was extracted with ethyl acetate (3×15 ml). The combined organic layers were washed with water (2×15 ml), dried over MgSO$_4$, and concentrated. The crude product was purified by flash chromatography (4:1 hexanes/ethyl acetate) and 40 mg of 3-cyclopropyl farnesol was obtained as a colorless oil.

II. Geranylgeraniol Analogs

Figure 5:
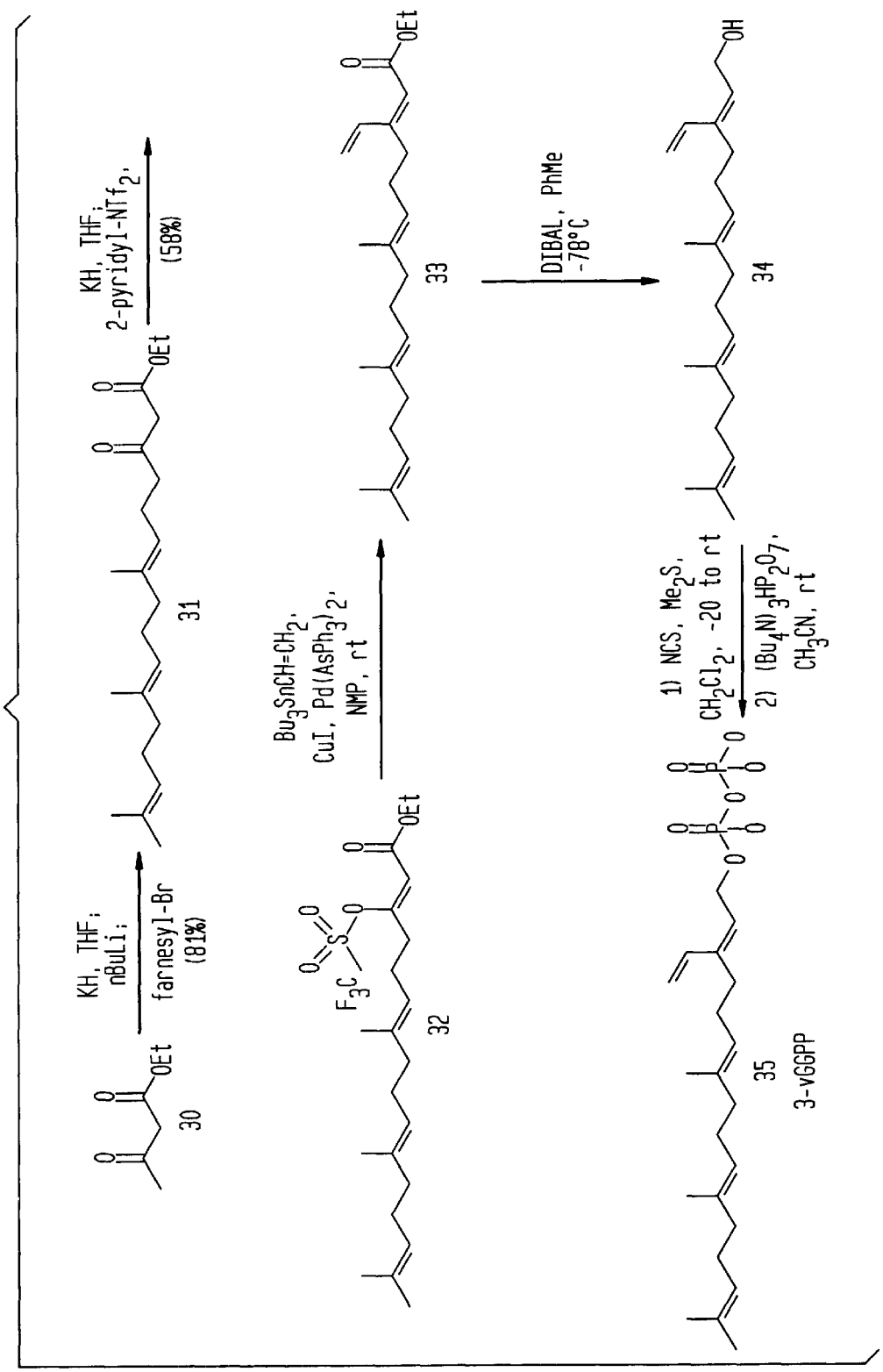
FIG. 5 is a reaction route for synthesizing 3-vinyl geranylgeranyl diphosphate (3-vGPP) and the corresponding 3-vinyl geranylgeraniol.

An illustrative reaction route for synthesizing 3-vinyl geranylgeranyl diphosphate (3-vGPP) and the corresponding 3-vinyl geranylgeraniol is shown in FIG. 5.

a. Vinyl Analogs

Ethyl 7,11,16-Trimethyl-3-oxohexadeca-6(E),10(E), 14-trienoate (Compound 31, β-keto ester)

To a suspension of KH (138 mg, 1.2 mmol) in 3.0 ml THF was added a solution of ethyl acetoacetate (0.064 ml, 0.5 mmol) in 1.0 ml THF at 0° C. under argon. After stirring for 20 minutes at room temperature, a clear colorless solution was formed. This solution was cooled to 0° C. and treated with n-butyllithium (1.7 M in hexane, 0.17 ml, 1.1 mmol). After 30 minutes at 0° C., farnesyl bromide (0.285 ml, 1.0 mmol, in 1.0 ml of THF) was added to the resulting dianion solution. Stirring was continued for an additional 30 minutes. The reaction mixture was quenched by adding ~3 ml of 10% aqueous citric acid, and extracted with ether (3×15 ml). The organic layers were combined, washed with saturated NaCl (2×15 ml) and dried over MgSO$_4$. After purification by flash chromatography (9:1 hexanes/ethyl acetate, R$_f$=0.40), the product 31 was obtained as a pale yellow oil (270 mg; 81% yield).

Ethyl 3-(Trifluoromethylsulfonyloxy)hexadeca-7,11, 15-trimethyl-2(Z),6(E),10(E),14-tetraenoate (Compound 32, Triflate)

KH (35% in mineral oil, 178 mg, 1.56 mmol) and 2.0 ml of THF was placed in a flame-dried, argon flushed flask. The β-ketoester (260 mg, 0.78 mmol) in 1.0 ml of THF was added to this suspension at 0° C. and stirred for 30 minutes. N-(2-Pyridyl)triflimide (349 mg, 0.94 mmol) in 1.0 ml of THF was added to the resulting enolate solution at 0° C. The reaction mixture was stirred at room temperature for 3 hours, quenched with ~5 ml of 10% aqueous citric acid, and extracted with ether (3×15 ml). The organic layers were combined, washed with 15 ml of 10% aqueous citric acid and 15 ml saturated NaCl solution, dried over MgSO$_4$, and concentrated. Purification by flash chromatography (20:1 hexanes/ethyl acetate) gave 185 mg (58% yield, based on consumed starting material) of the triflate (Compound 32) as a pale yellow oil, and 30 mg of recovered β-ketoester Compound 31.

Ethyl 3-Vinyl-7,11,15-trimethylhexadeca-2(Z),6(E), 10(E),14-tetraenoate (Compound 33)

In a flame dried, argon flushed flask were placed triflate (180 mg, 0.39 mmol), Pd(PhCN)$_2$Cl$_2$ (7.7 mg, 0.02 mmol), AsPh$_3$ (24 mg, 0.08 mmol), CuI (7.4 mg, 0.04 mmol) an 0.5 ml of NMP (99.5%, anhydrous). Vinylbutyltin (0.14 mg, 0.46 mmol) was added to this mixture, and stirred for 15 hrs at room temperature. The reaction mixture was taken up with 100 ml ethyl acetate and washed with aqueous KF (3×30 ml). The aqueous layer was back-extracted with ethyl acetate (2×15 ml) and the combined organic layers were dried over MgSO$_4$ Concentration followed by purification by flash chromatography (2:1 hexanes/ethyl acetate, R$_f$=0.53) gave Compound 33 as a colorless oil (98 mg, 73% yield). The identity, and in particular the stereochemistry, of this ester was confirmed by the similarity of its $^1$H-NMR spectrum to the previously prepared 3-vinyl-3-desmethylfarnesyl ester.

3-Vinyl-7,11,15-trimethylhexadeca-2(Z),6(E),10(E), 14-tetraen-1-ol (Compound 34)

To a solution of ester Compound 33 (95 mg, 0.28 mmol) in 2.0 ml of toluene was added diisobutyl aluminum hydride (1.0 M solution in toluene, 0.7 ml, 0.7 mmol) under argon at −78° C. The reaction was stirred at −78° C. for one hour and warmed to room temperature. The reaction was quenched by adding 30 ml of Rochelle salt solution. The aqueous solution was extracted with ethyl acetate (2×20 ml). The combined organic layers were washed with saturated NaCl (2×20 ml) and dried over MgSO$_4$. Concentration followed by flash chromatography (4:1 hexanes/ethyl acetate; R$_f$=0.45) afforded alcohol Compound 34 (52 mg, 62% yield) as a colorless oil.

Compound 35, 3-vGGPP, is made in accordance with the general procedures set forth hereinabove for converting the alcohol to the chloride and then to the diphosphate.

b. Allyl Analogs:

Ethyl 3-Allyl-7,11,15-trimethylhexadeca-2(Z),6(E), 10(E),14-tetraenoate

In a flame dried, argon flushed flask were placed triflate 32 (562 mg, 1.2 mmol), Pd(PhCN)$_2$Cl$_2$(23 mg, 0.061 mmol), AsPh$_3$(38 mg, 0.12 mmol), CuI (23 mg, 0.12 mmol) an 1.5 ml of NMP (995%, anhydrous). The flask was heated to 100° C. To this mixture was added allyltributyltin (0.76 ml, 2.4 mmol). After 15 hrs at 100° C., the reaction was cooled, taken up in 100 ml ethyl acetate and washed with aqueous KF (3×30 ml). The aqueous layer was back-extracted with ethyl acetate (2×15 ml) and the combined organic layers were dried over MgSO$_4$. Concentration, followed by purification by flash chromatography (98:2 hexanes/ethyl acetate) gave the ester as a colorless oil (222 mg, 52% yield).

3-Allyl-7,11,15-trimethylhexadeca-2(Z),6(E),10(E), 14-tetraen-1-ol

To the solution of ester (191 mg, 0.53 mmol) in 3.0 ml of toluene was added diisobutyl aluminum hydride (1.0 M solution in toluene, 1.5 ml, 1.5 mmol) under argon at −78° C. The reaction mixture was stirred at −78° C. for one hour and warmed to room temperature. The reaction was quenched by adding 30 ml of Rochelle salt solution. The aqueous solution was extracted with ethyl acetate (2×20 ml). The combined organic layers were washed with saturated NaCl (2×20 ml) and dried over $MgSO_4$. Concentration, followed by flash chromatography (9:1 hexanes/ethyl acetate) afforded the alcohol 3-allyl-geranylgeraniol (128 mg, 76% yield) as a colorless oil.

3-Allyl-7,11,15-trimethylhexadeca-2(Z),6(E),10(E), 14-tetraene diphosphate

This compound was prepared from alcohol via the corresponding chloride as described above in the general procedures and for 3-vinyl GGPP.

Experimental Procedures and Results

In vitro Prenyltransferase Assays

FTase $IC_{50}$ values of seven diphosphate analogs were determined using recombinant mFTase (affinity purified rat FPTase) in a scintillation proximity assay with tritiated FPP (specific activity 15–30 Ci/mmol, final concentration 0.12 $\mu$M) and the peptide Biotin-Aha-Thr-Lys-Cys-Val-Ile-Met-OH (final concentration 0.1 $\mu$M) as substrates. The method is described in detail in Yokama, et al., *J. Biol. Chem.*, Vol. 272, No. 7, pages 3944–3952 (February 1997). The FTase, tritiated FPP, and the peptide were incubated at 37° C. for 30 minutes in a buffer. After incubation, a stop reagent and streptavidin beads (Amersham) were added. The radioactive product was counted on a Wallac Microbeta 1450 scintillation counter. The kinetic fits were derived from a nonlinear least squares computer fit of the data. The $K_i$ values were determined using the same assay system with varying concentrations of tritiated FPP.

GGTase I values were determined in a similar manner using recombinant mGGTase I, tritiated GGPP, and the peptide Biotin-Aha-Thr-Lys-Cys-Val-Ile-Leu-OH.

The results of the prenyltransferase assays are shown in Table I:

TABLE 1

Inhibition Constants for FPP and GGPP Analogs[a]

| Analog | $IC_{50}$ FTase | $IC_{50}$ GGTase I | $K_1$ FTase | FTase/GGTase |
|---|---|---|---|---|
| 3-vFPP | 173 | ~100,000 | 96 | ~600 |
| 3-tbFPP | 31 | ~50,000 | 8.0 | ~1600 |
| 3-alFPP | 189 | >100,000 | 31 | >530 |
| 3-etFPP | 215 | >100,000 | — | >460 |
| 3-phFPP | 299 | >100,000 | — | >340 |
| 3-vGGPP | 715 | 3,050 | — | 4.3 |
| 3-alGGPP | 453 | 3,380 | — | 7.5 |

[a]Conditions: All inhibition constants are in nanomolar amounts. Values were determined using recombinant mFTase or recombinant mGGTase I in a scintillation proximity assay as appropriate.

Referring to Table 1, 3-tbFPP is a potent inhibitor of mFTase. The selectivity observed for mFTase against the closely related enzyme mGGTase I is also noteworthy, and is in accord with the ability of GGTase I to select for its proper isoprenoid, GGPP. The 3-substituted FPP analogs inhibited mFTase, albeit not as potently as 3-tbFPP. The three most potent inhibitors of mFTase (3-vFPP, 3-tbFPP, and 3-alFPP) were further characterized and were determined to all be competitive inhibitors of the enzyme versus FPP.

The geranylgeranylase analogs 3-vGGP and 3-alGGPP were surprising in their ability to bind more tightly to mFTase than to mGGTase I. This underscores the surprising difference in diphosphate binding selectivity between these two enzymes which are highly similar in amino acid sequence, and in fact, share an identical a subunit. It also emphasizes the highly selective nature of GGTase I and the difficulty in obtaining either peptide- or isoprenoid-based inhibitors of this enzyme that do not also inhibit mFTase.

Soft Agar Assays to Demonstrate Inhibition of Ras-transformed Cell Growth In vitro The isoprenyl diphosphate analogs are unstable and unlikely to penetrate cell membranes unaided, although the natural isoprenoids are apparently taken up by cells through an active transport system. Since it has been demonstrated that mammalian cells can utilize farnesol and geranylgeraniol for the prenylation of proteins, the 3-substituted isoprenoid alcohol analogs were used in this study to inhibit the anchorage-independent growth of transformed NIH3T3 fibroblasts. Presumably, the non-polar alcohols pass through the cell membrane and are then diphosphorylated by an as yet uncharacterized kinase to FPP or GGPP.

The 3-substituted analogs were evaluated as inhibitors of the growth of ras-transformed cells by comparing their relative degree of activity against an isogenic panel of transformed cell lines, comprised of NIH 3T3 fibroblasts transfected with either H-Ras(61 L) [H-Ras-F], H-Ras(61 L)CVLL [H-Ras-GG], or a transforming form of c-raf [Raf]. The H-Ras-F, H-Ras-GG, and raf transformed NIH3T3 cell lines have been previously described in Cox, et al., *Molecular and Cellular Biology*, Vol. 12, No. 6, pages 2606–2615 (1992). The cells were grown prior to plating in Dulbecco's modified Eagle medium supplemented with 10% calf serum and 1% antibiotic/antimycotic at 37° C. and 10% $CO_2$. Experiments were carried out in 6-well dishes in a two layer agar system (0.6% bottom layer and 0.3% top layer). Cells were incorporated into the top layer along with varying concentrations of the compound prepared in ethanol. Compound addition occurred only at the time the cells were seeded. Subsequent incubation was at 37° C. with 10% $CO_2$ for 2 weeks. Colonies were stained with 0.5 ml/well of 1 mg/ml p-iodonitrotetrazolium violet (Sigma) for 24 hours prior to quantitation by image analysis.

The results are shown below in Table 2. Of the six analogs tested, only the vinyl and allyl compounds exhibited cellular activity. Although not shown on Table 2, 3-tert-butylfarnesol proved to be inactive in cells, which may be due to the inability of the putative kinase to accept the bulky tert-butyl-substituted alcohol.

TABLE 2

Anchorage-Independent Growth Inhibition by Farnesol and Geranylgeraniol Analogs[a]
Mean $IC_{50}$ (±S.E.) ($\mu$M)

| Analog | H-Ras-F | H-Ras-GG | Raf |
|---|---|---|---|
| 3-vinyl Farnesol | 10.9 ± 2.6 (8) | 14.1 ± 1.4 (5) | 1.9 (1.3, 2.5) |
| 3-ally Farnesol | 10.2 ± 3.5 (3) | >25 (4) | 13.2 (10.3, 16.0) |

TABLE 2-continued

Anchorage-Independent Growth Inhibition by Farnesol and Geranylgeraniol Analogs[a]
Mean $IC_{50}$ (±S.E.) (μM)

| Analog | H-Ras-F | H-Ras-GG | Raf |
|---|---|---|---|
| 3-ethyl Farnesol | >25 (2) | >25 (2) | n.d. |
| 3-phenyl Farnesol | >25 (2) | >25 (2) | n.d. |
| 3-vinyl Geranylgeraniol | 18.0 ± 4.1 (5) | 13.9 ± 2.3 (4) | 5.6 (4.7, 6.4) |
| 3-allyl Geranylgeraniol | >25 (4) | 4.6 ± 1.9 (3) | >25 (2) |

[a]Conditions: Cells were assayed for inhibition of anchorage-independent growth as described above. The numbers in parentheses indicate the number of tests performed (H-Ras-F and H-Ras-GG) or the individual $IC_{50}$'s obtained from two tests (Raf). [n.d. = not determined]

The most striking selectivity was observed for 3-allylgeranylgeraniol, which exhibited an $IC_{50}$ of 4.6 μM against H-Ras-GG cells, but was totally ineffective ($IC_{50}$>25 μM) against both H-Ras-F and Raf cells. In contrast, 3-allylfarnesol exhibited the same degree of activity against the H-Ras-F and Raf lines, although it did prove to be ineffective against H-Ras-GG cells. When comparing the biological activities of the various analogs, H-Ras-F and Raf cells were uniformly more susceptible to 3-vinylfarnesol than 3-vinylgeranylgeraniol, whereas H-Ras-GG cells were equally inhibited by both compounds.

Subcellular Fractionation Experiments

The soft agar data presented hereinabove established the 3-vinyl and 3-allyl alcohol analogs as potent inhibitors of transformed cell growth. Surprisingly, neither 3-vinylfarnesol nor 3-vFPP blocked the prenylation of Ras proteins in H-Ras-F cells. This is contrary to the results seen with typical FTase inhibitors. Since the mechanism for the inhibition effect has not been firmly established, the ability of the corresponding diphosphates (3-vFPP and 3-alFPP) to inhibit FTase in vivo was investigated in a series of subcellular fractionation experiments.

H-Ras-F (A) or H-Ras-GG (B) cells were treated with 25 μM lovastatin for 24 h after which the indicated FPP or GGPP analogs (resuspended in media) were added directly to the cell media. Following an additional 24 h incubation period, the cells were harvested, lysed and the membranes (M) separated from the cytosol (C). After solubilization of the membrane fraction, Ras protein was immunoprecipitated from both the membrane and cytosolic fractions by the addition of the Y13-259 antibody (OP04 from Oncogene Science). The presence of Ras protein in each fraction was analyzed by Western transfer techniques. Incubation with the primary antibody (pan-ras Ab-2 from Oncogene Science) and an anti-mouse HRP conjugate secondary antibody (Amersham) was employed for detection of the ras protein. Blots were developed using Enhanced Chemiluminescence techniques (Amersham). The technique is described in detail by Scholten, et al., *Bioorg. Med. Chem.*, Vol. 4, pages 1537–1543 (1992).

Figure 6:
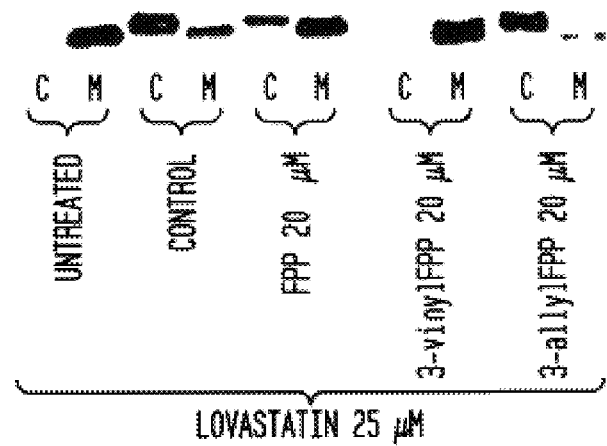
FIG. 6 is a Western blot showing the subcellular labeling of H-Ras in H-Ras-F cells.
Figure 7:
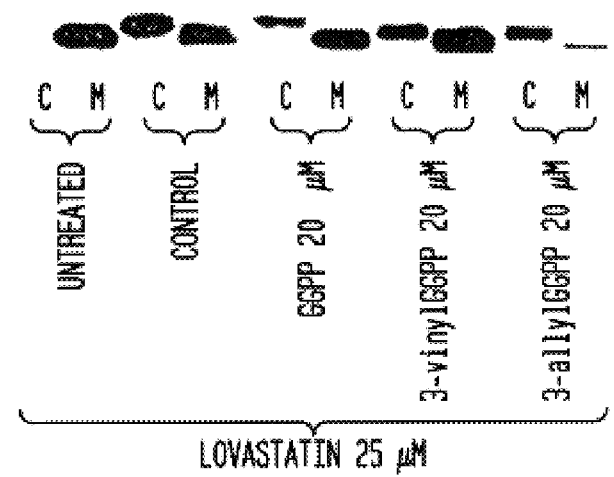
FIG. 7 is a Western blot showing the subcellular labeling of H-Ras of the H-Ras-GG cells.

The results are shown in FIGS. 6 and 7 which are Western blots of the H-Ras-F and H-Ras-GG experiments, respectively. H-Ras-F cells were treated with lovastatin in order to block the mevalonate pathway, prevent the formation of FPP and GGPP, and thus, inhibit protein prenylation. This inhibition is evidenced on the Western blot shown in FIG. 6 by a shift of the majority of H-Ras from the membrane fraction (M) to the cytosol (C), when compared with the DMSO control. The shift is significantly reversed by subsequent treatment of the cells with FPP. Dosing of the lovastatin-treated cells with 3-alFPP results in virtually all of the H-Ras being found in the cytosol. This is consistent with 3-alFPP acting as an FTase inhibitor rather than a substrate. In sharp contrast, dosing of the lovastatin-treated cells with 3-vFPP results in virtually complete localization of the H-Ras protein in the membrane fraction (M). Thus, it appears that 3-vFPP acts as an alternative substrate for FTase, leading to the formation of 3-vinylfarnesylated Ras.

Figure 8:
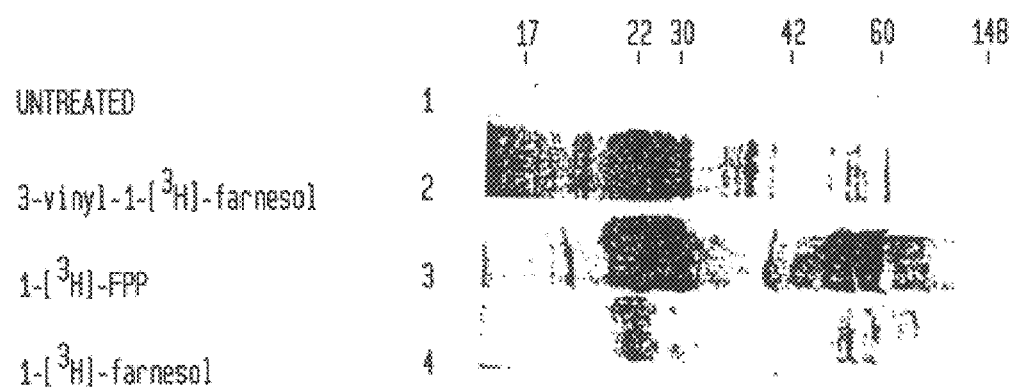
FIG. 8 shows the incorporation of a radiolabel into H-ras-F cells.

Further confirmation of these results was provided by treatment of H-Ras-F cells with tritium-labeled 3-vinylfarnesol. H-Ras-F cells were treated with 25 μM lovastatin for 24 h after which the following were added directly to four samples of the cell media: (1) control-untreated, (2) 3-vinyl-1-[$^3$H]-farnesol (5 μM, 1.34 μCi/ml), (3) 1-[$^3$H]-FPP (3 μM, 50 μCi/ml; Amersham), and (4) 1-[$^3$H]-farnesol (3 μM, 50 μCi/ml; American Radiolabeled Chemicals). Following an 18 h incubation period, the cells were lysed and the proteins were separated by SDS-PAGE on a 14% gel, and transferred to an Immobilon-P PVDF membrane (Millipore). After drying, the membranes were sprayed with En$^3$Hance (Amersham) and exposed to film (Hyperfilm MP, Amersham) for a period of time prior to developing (4 days for 1-[$^3$H]-FPP and 1-[$^3$H]-farnesol) and 28 days for 3-vinyl-1-[$^3$H]-farnesol). The exposed films are shown on FIG. 8 where the control and radioactive bands are designated as indicated above. Referring to FIG. 8, the radiolabel migrates with the same protein bands as seen when cells are treated with tritiated farnesol and FPP, verifying the farnesylation of these proteins by 3-vFPP.

The selectivity and mechanism of the observed cell growth inhibition was further probed by studying the effects of the 3-vinyl and 3-allyl GGPP analogs on the subcellular distribution of the geranylgeranylated protein variant in H-Ras-GG cells in a manner similar to that described for 3-vFPP and 3-alFPP. The Western blot is shown on FIG. 8. With H-Ras-GG cells, as with H-Ras-F cells, blockage of the mevalonate pathway results in a shift in the subcellular location of the Ras protein from the membrane to the cytosol. In accord with the results described above, dosing of lovastatin-treated H-Ras-GG cells with 3-vGGPP, but not 3-alGGPP, resulted in restoration of the membrane localization of H-Ras-GG.

It has been well established that levels of lovastatin that completely block the mevalonate pathway result in cell cycle blockade, significant cytotoxicity, and a sharp change in cell appearance to a rounded morphology. The effects of lovastatin on the cell morphology of H-Ras-F and H-Ras-GG cells treated with FPP, GGPP, 3-vFPP, 3-vGGPP, 3-alFPP, and 3-alGGPP were photographed and the results are shown on FIG. 9 (H-Ras-F) and 8 (H-Ras-GG), respectively. The H-Ras-F and H-Ras-GG cells were grown in six-well plates to 70–80% confluence. After treating the cells with lovastatin (25 μM) for 24 hour, the indicated FPP or GGPP analogs (re-suspended in media) were added directly to the cell media. Photographs were taken after an additional 24 hour incubation period.

Figure 9:
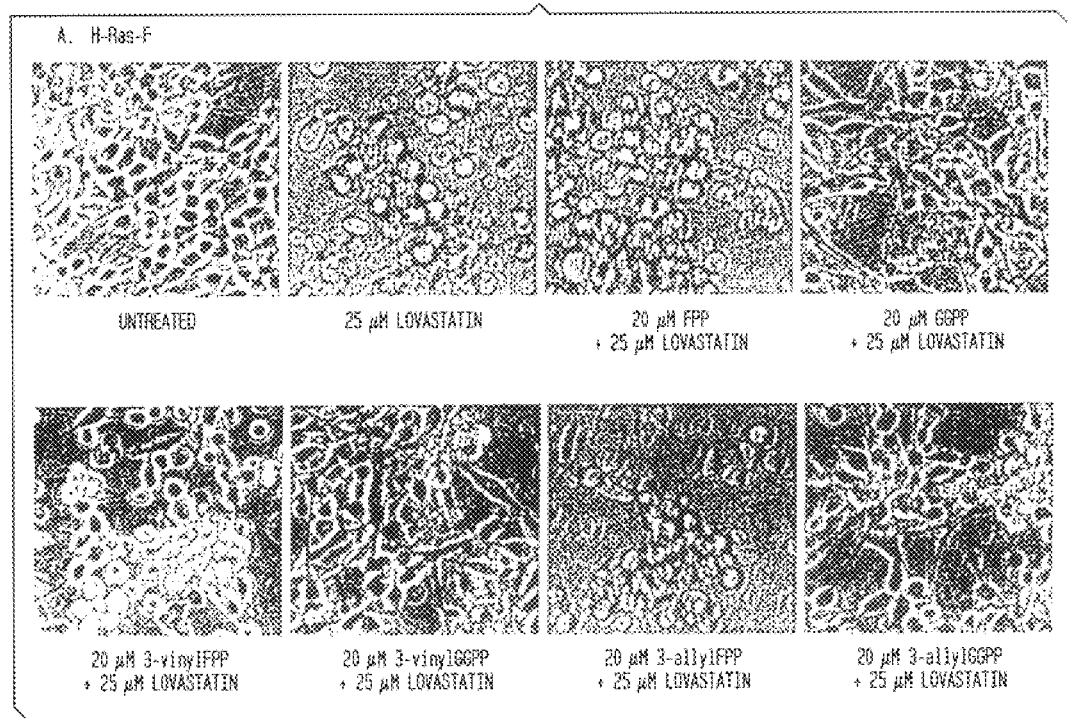
FIG. 9 shows photographs of the morphology of H-Ras-F cells treated with lovastatin and the indicated FPP analogs.
Figure 10:
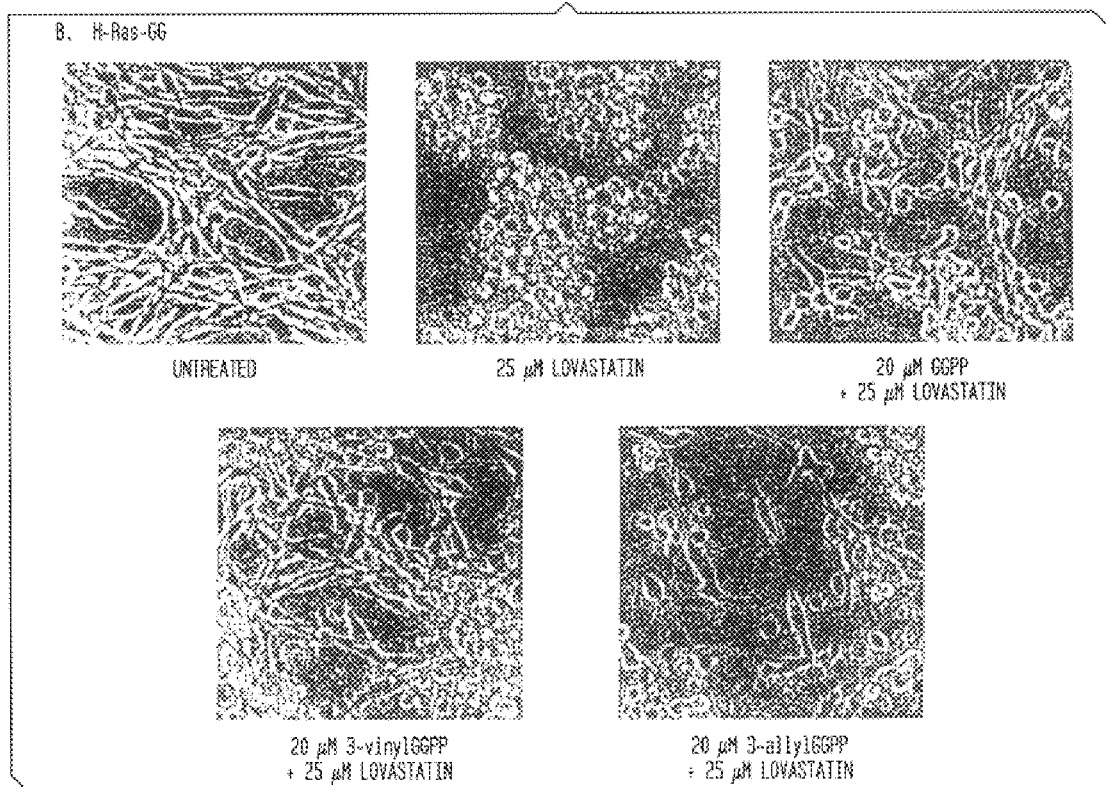
FIG. 10 shows photographs of the morphology of H-Ras-GG cells treated with lovastatin and the indicated GGPP.

The change in cell morphology can be reversed in lovastatin-treated H-Ras-F cells with geranylgeraniol or GGPP, but not farnesol or FPP, as demonstrated in FIG. 9. As expected, 3-alFPP was not able to reverse the morphology of lovastatin-treated cells; however, 3-vFPP exhibits a modest ability to do so. The ability of 3-vGGPP to restore the flattened morphology of cells is in accord with its ability to prenylate H-Ras-GG (See FIG. 7). However, the reversion in morphology seen with 3-alGGPP was completely unexpected. Furthermore, with lovastatin-treated H-Ras-GG cells, 3-vGGPP was able to completely restore, and 3-alGGPP was able to partially restore, the flattened morphology (FIG. 10). This indicates that 3-alGGPP can be used as a prenyl source by GGTase I with certain protein substrates, but not H-Ras(61 L)CVLL. An alternative explanation is that 3-alGGPP may serve as a substrate for GGTase II, and prenylation of these proteins may allow for morphological reversion of cells.

In conclusion, the data presented herein demonstrate that certain FPP analogs can act as potent inhibitors of mammalian FTase; farnesol and geranylgeraniol analogs can be prodrugs for the corresponding FPP and GGPP derivatives; and the prenyl alcohol derivatives potently inhibit the growth of ras-transformed cells via two different mechanisms. The selectivity of 3-allylfarnesol and 3-allylgeranylgeraniol in soft agar assays (Table 2) and their behavior in the subcellular fractionation experiments (FIGS. 6 and 7) are in accord with previous studies on FTase and GGTase I inhibitors. That is, they appear to block the growth of ras-transformed cells by preventing the prenylation of the Ras protein. It is striking and surprising, however, that 3-allylgeranylgeraniol exhibits such selectivity in cells, while 3-alGGPP exhibits no selectivity in vitro (see Table 1). Perhaps the intracellular level of GGPP is in the low nanomolar level in contrast to the much higher intracellular FPP concentration (~5 $\mu$M), and thus 3-alGGPP can compete effectively with the natural substrate for GGTase I but not FTase. Nevertheless, 3-allylgeranylgeraniol is a highly specific cellular inhibitor of protein geranylgeranylation, and thus may also be a valuable tool to investigate the relative biological importance of geranylgeranylation versus farnesylation.

In sharp contrast, 3-vinylfarnesol is converted to 3-vFPP, which acts as an alternative substrate for FTase and serves as a prenyl donor both in vitro and in vivo. The corresponding geranylgeranyl analog appears to act in the same manner. Thus, the observed biological activity of the vinyl substituted compounds is not due to FTase or GGTase I inhibition. While not wishing to be bound by theory, the activity could be due to inhibition of squalene synthase, cis-prenyltransferase, or trans-prenyltransferase, which utilize FPP to make cholesterol, dolichol and ubiquinone, respectively. Relatively high concentrations of farnesol have antiproliferative effects on cultured tumor cells. However, in control experiments 30 $\mu$M farnesol exhibited little effect on the proliferation of H-Ras-F cells (data not shown), in contrast to the complete inhibition of growth seen with 3-vinylfarnesol. In the studies presented below, 500 nM farnesol had no effect on HPAC cells whereas 500 nM 3-vinylfarnesol and 3-allylfarnesol were potently cytotoxic against HPAC cells in situ.

Effect of 3-Substituted Farnesols on the Proliferation of HPAC Cells

The malignant human cell line HPAC (human pancreatic adenocarcinoma cells) was used in this study. The cells were seeded at a concentration of 2×10$^5$/ml in 24 well culture plate (Costar, Cambridge, Mass). 3-Vinylfarnesol and 3-allylfarnesol were dissolved separately in 95% ethanol to make a stock solution. Varying amounts of the stock solutions were then used to treat the HPAC cells. The final concentration of the farnesol analogs in the culture plate wells ranged from 0 nM (ethanol-treated control) to 500 nM. The plate was then incubated at 37° C. under a 5% CO$_2$-humidified atmosphere for 48 hours. The total viable cells from each well were determined by Trypan Blue (0.4%) exclusion (Gibco, N.Y.) followed by cell counting. Under these conditions, 2.2×10$^6$ cells were found in the control well. With both 3-substituted analogs, treatment with 100 nM of the analog led to cytostasis (the cell count was roughly equal to 2×10$^5$/well) while treatment with 500 nM of the analog led to complete cytotoxicity (no viable cells remained in the well). Under the same conditions, 500 nM of the natural isoprenoid farnesol had no effect on the growth of HPAC cells, leading to the same cell count as the ethanol-treated control.

Preliminary In vivo Toxicity Studies

3-Vinylfarnesol and 3-allylfarnesol were dissolved in 95% ethanol and then diluted in normal saline. A 0.1 mg/kg dose of 3-vinylfarnesol was injected into a SCID mouse. No toxic response was seen after 48 hours, so a further 1 mg/kg dose was injected into the same mouse. Again, no adverse effects were seen after 48 hours, so an additional 10 mg/kg dose was given. No visible adverse effects were seen at any point during this treatment.

A 0.1 mg/kg dose of 3-allylfarnesol was injected into a second SCID mouse. No toxic response was seen after 48 hours, so a further 1 mg/kg dose was injected into this mouse. Again, no adverse effects were seen after 48 hours, so an additional 10 mg/kg dose was given. No visible adverse effects were seen at any point during this treatment.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:
1. The compound which is 7-allyfarnesol.
2. The compound which is para-biphenylfarnesol.
3. The compound which is 3-allylfarnesol.
4. The compound which is 3-isopropylfarnesol.
5. The compound which is 3-isopropylfarnesyl diphosphate.
6. The compound which is 3-allyl geranylgeranyl diphosphate.
7. A method for reducing the level of protein farnesylation in mammalian cells in a mammalian host, wherein said cells are sensitive to treatment with a compound selected from the group consisting of 3-vinyl farnesol, 3-allylfarnesol, 3-isopropylfarnesol, 3-vinyl geranylgeraniol, and 3-allylgeranylgeraniol; the said method comprising administering to said mammalian host an amount of the compound effective to inhibit the activity of farnesyl protein transferase; wherein the activity of farnesyl protein transferase is reduced.
8. A method for reducing the level of protein geranylgeranylation in mammalian cells in a mammalian host, wherein said cells are sensitive to treatment with a compound with the formula:

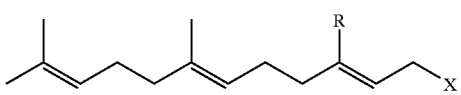

wherein R is a $C_2$–$C_{10}$ saturated or unsaturated alkyl, aryl, cycloalkyl, or $C_6$–$C_{10}$ aromatic or heteroaromatic group, and X is —OH or —$P_2O_7$; the said method comprising administering to said mammalian host an amount of the compound effective to inhibit the activity of geranylgeranyl protein transferase; wherein the activity of geranylgeranyl protein transferase is reduced.

9. The method of claim 8 wherein the compound is selected from the group consisting of 3-vinyl geranylgeraniol and 3-allylgeranylgeraniol.

10. A compound of the general formula:

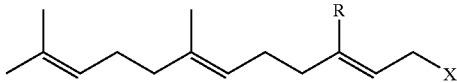

wherein R is selected from the group consisting of unsaturated isomers of propyl, butyl (exclusive of tert-butyl), and pentyl, cyclopentyl, and heterosubstituted moieties selected from the group consisting of fluorophenyl, (trimethylsilyl) methyl, 1-ethoxyvinyl, and 2-furanyl, 2-thiophenyl, and X is —OH or —$P_2O_7$.

11. A compound of the general formula:

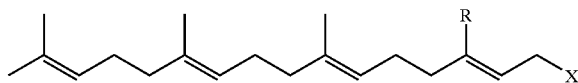

wherein R is selected from the group consisting of unsaturated isomers of propyl, butyl (exclusive of tert-butyl), and pentyl, cyclopentyl, and heterosubstituted moieties selected from the group consisting of fluorophenyl, (trimethylsilyl) methyl, 1-ethoxyvinyl, and 2-furanyl, 2-thiophenyl, and X is —OH or —$P_2O_7$.

12. A method of inhibiting restenosis by administering an effective amount of 3-allyl or 3-vinyl geranylgeraniol to a patient following cardiac catheterization or angioplasty.

* * * * *